United States Patent
Rodier et al.

(10) Patent No.: US 11,633,333 B2
(45) Date of Patent: Apr. 25, 2023

(54) SURFACTANT FOR WATER-IN-OIL EMULSION

(71) Applicant: GATTEFOSSÉ SAS, Saint-Priest (FR)

(72) Inventors: Jean-David Rodier, Villeurbanne (FR); Maxime Nollet, Lyons (FR)

(73) Assignee: GATTEFOSSÉ SAS, Saint-Priest (FR)

( * ) Notice: Subject to any disclaimer, the term of this patent is extended or adjusted under 35 U.S.C. 154(b) by 0 days.

(21) Appl. No.: 15/734,851

(22) PCT Filed: Jun. 11, 2019

(86) PCT No.: PCT/FR2019/051411
§ 371 (c)(1),
(2) Date: Dec. 3, 2020

(87) PCT Pub. No.: WO2019/239060
PCT Pub. Date: Dec. 19, 2019

(65) Prior Publication Data
US 2021/0228458 A1     Jul. 29, 2021

(30) Foreign Application Priority Data
Jun. 12, 2018    (FR) ..................... 1855115

(51) Int. Cl.
*A61K 8/36*       (2006.01)
*A61K 8/39*       (2006.01)
*A61K 8/06*       (2006.01)

(52) U.S. Cl.
CPC .............. *A61K 8/064* (2013.01); *A61K 8/361* (2013.01); *A61K 8/39* (2013.01); *A61K 2800/10* (2013.01); *A61K 2800/43* (2013.01); *A61K 2800/524* (2013.01); *A61K 2800/596* (2013.01)

(58) Field of Classification Search
None
See application file for complete search history.

(56) References Cited

U.S. PATENT DOCUMENTS

| | | | |
|---|---|---|---|
| 5,840,943 A | 11/1998 | Ansmann et al. | |
| 2015/0315123 A1 | 11/2015 | Schuch et al. | |
| 2016/0015609 A1* | 1/2016 | Merat | C08F 2/24 424/59 |

FOREIGN PATENT DOCUMENTS

| | | |
|---|---|---|
| FR | 2936154 A1 | 3/2010 |
| JP | 2008119568 A | 5/2008 |
| JP | 2011079753 A | 4/2011 |
| JP | 2011193734 A | 10/2011 |
| WO | 2007/027447 A1 | 3/2007 |
| WO | 2018/191585 A1 | 10/2018 |

OTHER PUBLICATIONS

International Search Report (and English translation) and Written Opinion of the International Searching Authority for International Application No. PCT/FR2019/051411 dated Oct. 28, 2019.
International Preliminary Report on Patentability for International Application No. PCT/FR2019/051411 dated. Mar. 16, 2020.
Griffin, W.C., "Classification of Surface-Active Agents by HLB'", Journal of the Society of Cosmetic Chemists 1 (1949): 311-326.

* cited by examiner

*Primary Examiner* — Jennifer A Berrios
(74) *Attorney, Agent, or Firm* — Heslin Rothenberg Farley & Mesiti P.C.

(57) ABSTRACT

The present invention relates to a water-in-oil surfactant consisting of a mixture of compounds of formula (I):

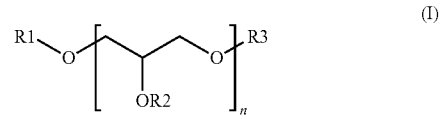

wherein the compound of formula (I) has an average degree of polymerisation n of between 4 and 6, R1, R2 and R3 being, independently of one another, a hydrogen atom or a group R4 derived from at least one carboxylic acid, the carboxylic acid being 12-hydroxystearic acid or a mixture of 12-hydroxystearic acid and ricinoleic acid.

The present invention also relates to a surfactant composition and to a cosmetic composition comprising this surfactant.

20 Claims, No Drawings

SURFACTANT FOR WATER-IN-OIL EMULSION

CROSS REFERENCE TO RELATED APPLICATIONS

This application is a national stage filing under section 371 of International Application No. PCT/FR2019/051411 filed on Jun. 11, 2019, and published on Dec. 19, 2019 as WO 2019/239060, which claims priority to French Application No. 1855115, filed on Jun. 12, 2018. The entire contents of WO 2019/239060 are hereby incorporated herein by reference.

FIELD OF THE INVENTION

The present invention relates to a surfactant for formulating water-in-oil emulsions obtained from fatty acids and polyglycerol having an average degree of polymerisation of between 4 and 6.

The field of use of the present invention in particular relates to the formulation of cosmetic compositions.

PRIOR ART

In general, the preparation of a water-in-oil type emulsion requires the use of a surfactant. More specifically, in the absence of a surfactant, the emulsion is generally unstable over time and results in the formation of a composition having two phases separated by an interface.

The surfactant allows the dispersion of a water phase in an oil phase to be stabilised. For this purpose, it comprises a hydrophobic part that is larger than a hydrophilic part.

By way of example, glycerol- and fatty carboxylic acid-based surfactants have been developed. In this respect, 12-hydroxystearic acid and ricinoleic acid are of particular interest insofar as they have a hydroxyl function that allows for self-polycondensation of the acids. The surfactant is then obtained by esterification of the compounds resulting from this polycondensation on the glycerol.

The hydrophobic part of the surfactant corresponds to the polycondensated acid residues whereas the hydrophilic part corresponds to the glycerol residue.

These surfactants allow various types of cosmetic products to be formulated, such as foundations containing pigments or compositions containing organic or mineral sun filters.

The U.S. Pat. No. 5,840,943 describes a water-in-oil emulsifier obtained by esterification of 12-hydroxystearic acid in the presence of a mixture of glycerol, diglycerol, triglycerol, tetraglycerol, pentaglycerol and oligoglycerol.

The U.S. patent No. 2015/315123 describes a water-in-oil emulsifier obtained by esterification of a C6-C22 carboxylic acid in the presence of a polyglycerol having an average degree of polymerisation of between 2 and 16.

The international patent No. 2007/027447 also describes a water-in-oil emulsifier obtained by esterification of a carboxylic acid in the presence of a polyglycerol, for example between ricinoleic acid and polyglycerol-3.

Given that the polyglycerol is obtained by polycondensation of glycerol, it generally contains glycerol and a mixture of polyglycerols having different degrees of polymerisation. Thus, the emulsifiers obtained from polyglycerol contain a mixture of esterified glycerol and of esterified polyglycerols.

Even though these emulsifiers allow stable water-in-oil emulsions to be prepared, there remains a need to procure emulsifiers which increase the stability of these emulsions, both at ambient temperature and at temperatures of about 40° C.

Surprisingly, the Applicant has overcome this problem by reducing or eliminating the presence of glycerol during the formation of an emulsifier from polyglycerol and one or more fatty carboxylic acids.

DESCRIPTION OF THE INVENTION

The surfactant according to the invention is a polyglycerol- and fatty acid-based surfactant, the acid being of the type 12-hydroxystearic acid ($CH_3$—$(CH_2)_5$—$CH(OH)$—$(CH_2)_{10}$—$C(=O)OH$) or a mixture of 12-hydroxystearic acid and ricinoleic acid ($CH_3$—$(CH_2)_5$—$CH(OH)$—$CH_2$—$CH=CH$—$(CH_2)_7$—$C(=O)OH$).

The polyglycerol used to prepare this surfactant has an average degree of polymerisation (DP) of between 4 and 6, i.e. a macromolecule comprising, on average, between four and six glycerol units —$(CH_2$—$CH(OH)$—$CH_2$—$O)$—.

The degree of polymerisation corresponds to the number-average degree of polymerisation, which is equal to the ratio of the number-average molecular weight of polyglycerol to the molecular weight of the glycerol unit (M=74 g/mol).

This surfactant procures emulsions having greater stability than those obtained with a surfactant prepared from glycerol or polyglycerol having an average degree of polymerisation of less than 4 or greater than 6.

In general, polyglycerols contain a non-negligible quantity of glycerol, the presence whereof is not an obstacle when preparing surfactants of the water-in-oil type. However, the Applicant has observed that, in an entirely unexpected manner, the surfactants prepared in the presence of at least 3 wt % glycerol do not procure emulsions that are stable over time.

More specifically, the invention relates to a water-in-oil surfactant consisting of a mixture of compounds of formula (I):

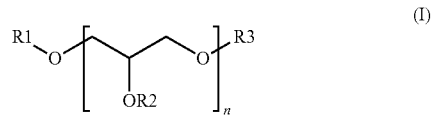

wherein the compound of formula (I) has an average degree of polymerisation n of between 4 and 6, R1, R2 and R3 being, independently of one another, a hydrogen atom or an R4 group derived from at least one carboxylic acid, the carboxylic acid being 12-hydroxystearic acid or a mixture of 12-hydroxystearic acid and ricinoleic acid, R4 being a group $C(=O)$—(R5)-$CH(OH)$—$(CH_2)_5$—$CH_3$ or $C(=O)$—(R5)-$CH[(CH_2)_5$—$CH_3]$—O—$\{C(=O)$—(R5)-$CH[(CH_2)_5$—$CH_3]$—$O\}_p$$C(=O)$—(R5)-$CH[(CH_2)_5$—$CH_3]$—OH where p=0 to 5, advantageously 0 to 3, more advantageously 0 to 2, R5 being a group $(CH_2)_{10}$ or a mixture of the groups $(CH_2)_{10}$ and $(CH_2)_7$—$(CH=CH)$—$CH_2$, at least one of the R1, R2 and R3 groups being an R4 group.

p is advantageously an integer from 0 to 5, more advantageously from 0 to 3, and even more advantageously from 0 to 2.

The structure of R4 can be presented as follows:

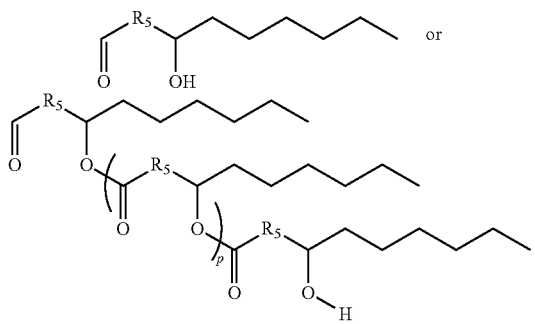

The water-in-oil surfactant according to the invention is the result of the esterification reaction between polyglycerol and one or more carboxylic acids, also capable of being esterified by self-polycondensation of the acids. These two types of esterification occur simultaneously.

The compound of formula (I) has an average degree of polymerisation n of between 4 and 6, advantageously between 4 and 5, more advantageously from 4.5 to 5. The number-average degree of polymerisation is determined by gas chromatography with flame-ionisation detection.

The surfactant according to the invention has a HLB value advantageously of between 1 and 6, more advantageously of between 2 and 6, and even more advantageously of between 3 and 5.

In general, the HLB value corresponds to the hydrophilic-lipophilic balance of the surfactant. It varies from 0 to 20, values of less than 6 correspond to surfactants that can be used to formulate water-in-oil emulsions, values greater than 8 correspond to surfactants that can be used to formulate oil-in-water emulsions. It is determined according to the Griffin method (Griffin W C, Classification of Surface Active Agents by HLB, Journal of the Society of Cosmetic Chemists, 1949, 1, pages 311-326).

The compound of formula (I) comprises at least one R4 group which is a derivative of 12-hydroxystearic acid or of a mixture of 12-hydroxystearic acid and ricinoleic acid. It can comprise a plurality of R4 groups that are identical to or different from one another.

Advantageously, the R1 and R3 groups are R4 groups.

When R4 is a group $C(=O)-(R5)-CH[(CH_2)_5-CH_3]-O-\{C(=O)-(R5)-CH[(CH_2)_5-CH_3]-O\}_p C(=O)-(R5)-CH[(CH_2)_5-CH_3]-OH$, p is an integer advantageously between 0 and 5, more advantageously between 0 and 3.

Since the compound of formula (I) has an average degree of polymerisation of between 4 and 6, it comprises, on average, between 4 and 6 R2 groups, advantageously between 4 and 5, more advantageously from 4.5 to 5. These R2 groups can be a hydrogen atom and/or an R4 group. All of the R2 groups are advantageously a hydrogen atom. In such a case, only the terminal OH groups of the polyglycerol can advantageously be esterified and correspond to R4.

In the formula (I), the mole ratio of the R4 groups (in R1 and/or R2 and/or R3 position) to the units ($-CH_2-CH(O+CH_2-O-)$) of polyglycerol is advantageously between 1 and 6, more advantageously between 2 and 4.

12-hydroxystearic acid and ricinoleic acid have the particularity of both comprising a hydroxyl OH function and a carboxylic acid COOH function. These two types of functions can react with one another by esterification (polycondensation) resulting in the formation of a macromolecule of carboxylic acid or of a mixture of carboxylic acids.

As stated hereinabove, this polycondensation reaction occurs simultaneously with the polyglycerol esterification reaction. In such a case, the R4 group is advantageously a mixture of groups in which $R5=(CH_2)_{10}$ and/or $(CH_2)_7-(CH=CH)-CH_2$.

Thus, when the surfactant according to the invention is prepared from a mixture of 12-hydroxystearic acid and ricinoleic acid, the R4 group can comprise R5 groups of the type $(CH_2)_{10}$ (12-hydroxystearic acid) as well as R5 groups of the type $(CH_2)_7-(CH=CH)-CH_2$ (ricinoleic acid).

The surfactant can take the form of an ABA-type block copolymer. This is in particular the case when R2 is a hydrogen atom and when R1 and R3 are both a poly(12-hydroxystearic acid) or a poly(ricinoleic acid).

When a mixture of carboxylic acids is implemented, the ratio of the number of R5 groups of the type $(CH_2)_{10}$ (12-hydroxystearic acid) to the number of R5 groups of the type $(CH_2)_7-(CH=CH)-CH_2$ (ricinoleic acid) is advantageously between 0.5 and 4, more advantageously between 0.75 and 2, even more advantageously between 1 and 2.

The surfactant according to the invention can be in solid form or viscous liquid form. However, the simultaneous presence of 12-hydroxystearic acid residues and of ricinoleic acid residues allows the nature of the surfactant to be modified, for example by making it viscous or fluid.

According to one specific embodiment, $R5=(CH_2)_{10}$. In other words, R4 is a derivative of 12-hydroxystearic acid, and more particularly a group $C(=O)-(CH_2)_{10}-CH(OH)-(CH_2)_5-CH_3$ or a poly(12-hydroxystearic acid) of the formula $C(=O)-(CH_2)_{10}-CH[(CH_2)_5-CH_3]-O-\{C(=O)-(CH_2)_{10}-CH[(CH_2)_5-CH_3]-O\}_p C(=O)-(CH_2)_{10}-CH[(CH_2)_5-CH_3]-OH$.

According to another specific embodiment, R5 can be a mixture of the groups $(CH_2)_{10}$ and $(CH_2)_7-(CH=CH)-CH_2$. In other words, R4 is a derivative of ricinoleic acid and of 12-hydroxystearic acid, and more particularly a mixture of the groups $C(=O)-(CH_2)_7-(CH=CH)-CH_2-CH(OH)-(CH_2)_5-CH_3$ and $C(=O)-(CH_2)_{10}-CH[(CH_2)_5-CH_3]-O-\{C(=O)-(CH_2)_{10}-CH[(CH_2)_5-CH_3]-O\}_p C(=O)-(CH_2)_{10}-CH[(CH_2)_5-CH_3]-OH$ or a poly(ricinoleic acid-12-hydroxystearic acid).

According to another specific embodiment, R2 is a hydrogen atom, and R1 and R3 are, independently of one another, a poly(12-hydroxystearic acid), a poly(ricinoleic acid) or a poly(12-hydroxystearic acid-ricinoleic acid).

Thus, R1 and R3 can be R4 groups of the formula $C(=O)-(CH_2)_{10}-CH[(CH_2)_5-CH_3]-O-\{C(=O)-(CH_2)_{10}-CH[(CH_2)_5-CH_3]-O\}_p C(=O)-(CH_2)_{10}-CH[(CH_2)_5-CH_3]-OH$ and/or of the formula $C(=O)-(CH_2)_7-(CH=CH)-CH_2-CH[(CH_2)_5-CH_3]-O-\{C(=O)-(CH_2)_7-(CH=CH)-CH_2-CH[(CH_2)_5-CH_3]-O\}_p C(=O)-(CH_2)_7-(CH=CH)-CH_2-CH[(CH_2)_5-CH_3]-OH$.

The use of a mixture of carboxylic acids allows the appearance of the surfactant to be modified, for example by making it more viscous, or even liquid at ambient temperature (20° C.). Thus, this embodiment can be particularly attractive for the preparation of water-in-oil emulsions at temperatures advantageously between 10 and 40° C., more advantageously between 15 and 30° C.

The present invention further relates to a method for preparing this surfactant via an esterification reaction between polyglycerol and at least one carboxylic acid. The carboxylic acid is 12-hydroxystearic acid or a mixture of 12-hydroxystearic acid and ricinoleic acid.

The polyglycerol has a number-average degree of polymerisation of between 4 and 6. It has a number-average molecular weight of advantageously between 314 g/mol and 462 g/mol. Moreover, it advantageously comprises less than 3 wt % glycerol (HO—CH$_2$—CH(OH)—CH$_2$—OH), more advantageously less than 2 wt %, and even more advantageously less than 1 wt %, by weight relative to the weight of the polyglycerol (DP n=4 to 6).

The polyglycerol is preferentially free of glycerol.

The esterification reaction is advantageously carried out in the presence of a polyglycerol/carboxylic acid(s) mole ratio of between 1 and 0.15, more advantageously between 0.5 and 0.25.

When a mixture of carboxylic acids is used, the 12-hydroxystearic acid/ricinoleic acid mole ratio is advantageously between 0.5 and 4, more advantageously between 0.75 and 2.

The esterification reaction is advantageously carried out at a temperature of between 185 and 235° C., more advantageously of between 190 and 220° C.

In general, the water generated during the formation of the surfactant can be removed, in a continuous or discontinuous manner, during the reaction, for example in a nitrogen flow. This prevents the backward esterification phenomenon.

On the other hand, the method can be carried out in the presence of a catalyst, for example hydroxide ions for the esterification of polyglycerol.

The method for preparing the surfactant according to the invention is advantageously carried out in the absence of a solvent.

As stated hereinabove, the polycondensation reaction for the one or more carboxylic acids occurs at the same time as the polyglycerol esterification reaction.

The present invention further relates to a surfactant composition comprising the surfactant according to the invention. This composition is produced from polyglycerol having an average degree of polymerisation of between 4 and 6. It is advantageously produced in the presence of less than 3 wt % glycerol (HO—CH$_2$—CH(OH)—CH$_2$—OH), advantageously less than 2 wt %, and more advantageously less than 1 wt %, by weight relative to the weight of the polyglycerol (DP n=4 to 6).

As stated hereinabove, reducing the quantity of glycerol increases the stability of the emulsions prepared from the surfactant or the surfactant composition according to the invention.

The surfactant and the surfactant composition according to the invention can be used to formulate water-in-oil emulsions, in particular in the cosmetics sector.

Moreover, the present invention further relates to a cosmetic composition comprising this surfactant or this surfactant composition.

The invention and the advantages procured thereby will be better understood upon reading the following examples provided for illustration purposes and not intended to limit the scope of the invention.

EXAMPLE EMBODIMENTS OF THE INVENTION

In general, GC-FID (gas chromatography with flame-ionisation detection) analyses were carried out to determine the composition of the polyglycerols used and thus the degree of polymerisation thereof, also noted DPn.

Example 1: Surfactant According to the Invention Prepared from 12-Hydroxystearic Acid and Polyglycerol (DPn=4.6)

378.6 g of 12-hydroxystearic acid and 121.4 g of polyglycerol were placed in a reactor. The reaction medium was heated to 210° C. under a nitrogen atmosphere. The water produced by the esterification reaction was removed in a nitrogen flow to shift the equilibrium. After 6 hours of reaction, the reactor was emptied and the reaction product (surfactant) was filtered through a polypropylene membrane.

This product was implemented in a water-in-oil emulsion in the manner described in Table 1. It was in solid form at 20° C.

TABLE 1

Composition of the formulation prepared using example 1.

| Ingredients | Weight percentage |
|---|---|
| Surfactant according to example 1 | 5 |
| Dicaprylyl carbonate | 25 |
| Preservative: phenoxyethanol and ethylhexylglycerin (90%/10% by weight) | 1 |
| Water | 68 |
| NaCl | 0.5 |
| MgSO$_4$ | 0.5 |

The Preparation Protocol for this Emulsion was as Follows:

The surfactant (example 1) was dissolved in the oil phase (dicaprylyl carbonate) and the two salts (NaCl, MgSO$_4$) were dissolved in water. The two phases were then heated to 75° C. in a water bath. Once the temperature was reached, the oil phase was stirred using a homogeniser at 2,000 rpm. The aqueous phase was then slowly added to the oil phase. Once this addition was complete, homogenisation at 2,000 rpm was maintained for 20 minutes. The emulsion was then placed in a cold water bath (20° C.) to reduce the temperature of the emulsion to 30° C. During placement in the cold water bath, the preservative was added drop by drop and stirring was reduced to 1,500 rpm. Stirring was then maintained for 10 minutes. The emulsion was then placed in a container to monitor stability.

The stability of this emulsion was monitored at ambient temperature, at 40° C. and after two formulation freeze/thaw cycles (Table 2).

TABLE 2

Stability of the formulation prepared using example 1.

| Conditions | Observations |
|---|---|
| Ambient temperature | Stable for at least 3 months |
| 40° C. | Stable for at least 1 month |
| Freeze/thaw cycle | Stable |

Examples 2 to 4: Surfactants Prepared from a Mixture of Carboxylic Acids and Polyglycerol (DPn=4.6)

The use of a mixture of 12-hydroxystearic acid and ricinoleic acid procures a viscous product that is easier to handle than the surfactant according to example 1. The surfactant thus obtained can be used to produce formulations at cold temperatures (between 20 and 25° C.).

Example 2 according to the invention: 171.2 g of ricinoleic acid, 172.6 g of 12-hydroxystearic acid and 121.4 g of polyglycerol were placed in a reactor. The reaction medium was heated to 210° C. under a nitrogen atmosphere. The water produced by the esterification reaction was removed in a nitrogen flow to shift the equilibrium. After 6 hours of reaction, the reactor was emptied and the reaction product (surfactant) was filtered through a polypropylene membrane.

The comparative examples 3 and 4 were produced according to the protocol in example 2, however with the following changes:
Example 3: 5% of the weight of the polyglycerol was replaced with glycerol.
Example 4: 30% of the weight of the polyglycerol was replaced with glycerol.

TABLE 3

Composition of the emulsions prepared using examples 2 to 4.

| Ingredients | Weight percentage |
| --- | --- |
| Surfactant according to example 2, 3 or 4 | 5 |
| Medium-chain triglycerides | 25 |
| Preservative: phenoxyethanol and ethylhexylglycerin (90%/10% by weight) | 1 |
| Water | 67 |
| NaCl | 1 |
| $MgSO_4$ | 1 |

The protocol for preparing these emulsions is identical to that in example 1.

The stability of the emulsions obtained using examples 2, 3 and 4 was monitored using an appliance of the Turbiscan™ type (Table 3). This appliance measures the average backscattering percentage of each composition. The higher the percentage, the opaquer and thus the finer the emulsion. Changes to this percentage denote a change in the formulation and thus in the stability thereof (Table 4).

TABLE 4

Stability of the emulsions prepared using examples 2 to 4.

| Surfactant | example 2 | example 3 | example 4 |
| --- | --- | --- | --- |
| Weight percentage of glycerol added to the polyglycerol | 0 | 5 | 30 |
| Average backscattering (%) | | | |
| T0 | 86.1 | 83.3 | 68.8 |
| 24 hours at 40° C. | 84.2 | 63.2 | 47.5 |
| 1 week at 40° C. | 78.3 | 40.7 | 48.2 |
| Normalised average backscattering (%) | | | |
| T0 | 100.0 | 100.0 | 100.0 |
| 24 hours at 40° C. | 97.8 | 75.9 | 69.0 |
| one week at 40° C. | 90.9 | 48.9 | 70.1 |

The emulsion obtained from the surfactant according to the comparative example 4 is less opaque at T0 than the other compositions. The emulsion is not as fine.

By normalising the average backscattering values, it can be seen that the formulae produced with the surfactants in the comparative examples 3 and 4 show a more significant drop in the average backscattering than those obtained in example 2 according to the invention.

In conclusion, the surfactants in the comparative examples 3 and 4 do not stabilise the formula as well as the surfactant in example 2 according to the invention.

In other words, the surfactants prepared from polyglycerol that is free from glycerol give more stable emulsions than the surfactants prepared from polyglycerol comprising 5% or 30% glycerol.

Examples 5 and 6: Surfactants Prepared from Polyglycerol 3.1 or Polyglycerol 4.6

The effect of the composition of the polyglycerol on the performance levels of the polyhydroxystearate esters thereof in the formulation was analysed.

Firstly, GC-FID (gas chromatography with flame-ionisation detection) analyses were carried out to determine the composition of two polyglycerols of different degrees of polymerisation. The results are given in Table 5.

TABLE 5

Composition of the polyglycerols A and B obtained by gas chromatography

| | Composition (%) | |
| --- | --- | --- |
| | polyglycerol A | polyglycerol B |
| glycerol | 2.17 | 0.14 |
| diglycerol | 23.68 | 9.47 |
| polyglycerol-3 | 48.35 | 27.44 |
| polyglycerol-4 | 18.28 | 21.71 |
| polyglycerol-5 | 5.63 | 14.46 |
| polyglycerol-6 | 1.56 | 9.81 |
| polyglycerol-7 | 0.32 | 6.82 |
| polyglycerol-7 | 0.02 | 4.59 |
| polyglycerol-9 | 0 | 2.87 |
| polyglycerol-10 to polyglycerol-13 | 0 | 2.72 |
| Mn (g/mol) | 245.63 | 359.12 |
| DPn (number of glycerol units) | 3.1 | 4.6 |

Polyglycerol B was also used to carry out examples 1 to 4.

Two surfactants were then synthesised from polyglycerols A and B according to the following protocol:

Example 5: 414.5 g of 12-hydroxystearic acid and 85 g of polyglycerol A were placed in a reactor. The reaction medium was heated to 215° C. under a nitrogen atmosphere. After 6 hours of reaction, the reactor was emptied and the ester was filtered through a polypropylene membrane.

Example 6 according to the invention: 359 g of 12-hydroxystearic acid and 140.5 g of polyglycerol B were placed in a reactor. The reaction medium was heated to 215° C. under a nitrogen atmosphere. After 5 hours of reaction, the reactor was emptied and the ester was filtered through a polypropylene membrane.

It should be noted that the weights of the fatty acid and polyglycerol in examples 5 and 6 were selected in order to keep an equivalent mole ratio of the acid to the polyglycerol in the two examples.

The two surfactants thus obtained were implemented in a water-in-oil formula (Table 6).

TABLE 6

Composition of the emulsions prepared using the surfactants in examples 5 and 6.

| Ingredients | Weight percentage |
|---|---|
| Surfactant in example 5 or 6 | 5 |
| Dicaprylyl carbonate | 25 |
| Preservative: phenoxyethanol and ethylhexylglycerin (90%/10% by weight) | 1 |
| Water | 68 |
| NaCl | 0.5 |
| $MgSO_4$ | 0.5 |

The Preparation Protocol for the Formulae was as Follows:

The surfactant was dissolved in the oil phase and the two salts were dissolved in water. The two phases were then heated to 75° C. in a water bath. Once the temperature was reached, the oil phase was stirred using a homogeniser at 2,000 rpm (revolutions per minute). The aqueous phase was then slowly added to the oil phase. Once the addition of water was complete, homogenisation at 2,000 rpm was maintained for 20 minutes. The emulsion was then placed in a cold water bath (20° C.) to reduce the temperature of the emulsion to 30° C. During placement in the cold water bath, the preservative was added drop by drop and stirring was reduced to 1,500 rpm. Stirring was then maintained for 10 minutes. The emulsion was then placed in a container to monitor stability.

The stability of the two formulations was monitored at ambient temperature, at 40° C. and after two formulation freeze/thaw cycles.

The results are given in Table 7.

TABLE 7

Stability of the formulations prepared using the surfactants in examples 5 and 6.

| Surfactant | Example 5 | Example 6 |
|---|---|---|
| Ambient temperature | Stable for less than one month | Stable for more than 3 months |
| 40° C. | Stable for less than 3 days | Stable for more than 7 days |
| Freeze/thaw cycle | Stable | Stable |

The stability of the formulations using surfactant B (derived from polyglycerol B) according to the invention is higher, regardless of the observation conditions. However, the formulation comprising surfactant A (derived from polyglycerol A) is clearly less stable.

The composition of the initial polyglycerol thus has a significant effect on the performance of the surfactant. The presence of glycerol or polyglycerol with a low degree of polymerisation (less than 4) inhibits the performance of the surfactant. Use of a polyglycerol with a number-average degree of polymerisation DP of between 4 and 6 is thus preferable.

Example 7: Surfactants Prepared from Polyglycerol 3.1 or Polyglycerol 10 (DPn=10)

Example 7: 323.26 g of 12-hydroxystearic acid and 151.7 g of polyglycerol C of DPn=10 were placed in a reactor. The catalyst was added under stirring. The reaction medium was heated under a nitrogen atmosphere. Heating was stopped when the acid number was lower than 2 mgKOH/g. The reactor was emptied and the ester was filtered through a polypropylene membrane.

This product was implemented in a water-in-oil formula (Table 8).

TABLE 8

Composition of the emulsion prepared using the surfactant in example 7.

| Ingredients | Weight percentage |
|---|---|
| Surfactant in example 7 | 5 |
| Dicaprylyl carbonate | 25 |
| Preservative: phenoxyethanol and ethylhexyl glycerin (90%/10% by weight) | 1 |
| Water | 68 |
| NaCl | 0.5 |
| $MgSO_4$ | 0.5 |

The protocol for preparing this formula is identical to that described for examples 5 and 6. The results are given in Table 9.

TABLE 9

Stability of the formulation prepared using the surfactant in example 7

| Surfactant | Example 7 |
|---|---|
| Ambient temperature | Stable for less than one month |
| 40° C. | Stable for less than 7 days |
| Freeze/thaw cycle | unstable |

The stability of the formula using the surfactant in example 7 is lower, regardless of the observation conditions, than that of the surfactants in examples 5 and 6 (see Table 7).

To summarise, the composition of the polyglycerol has a significant effect on the performance of the formulations. The initial presence of polyglycerol with a small or large degree of polymerisation inhibits the performance of the surfactant. Use of a polyglycerol with a degree of polymerisation DPn of between 4 and 6 is thus preferable, i.e. having a molecular weight of between 314 g/mol and 462 g/mol.

Effect of the Degree of Polymerisation of Polyglycerol or of the Composition of Hydroxy Fatty Acid on the Performance Levels of the Esters Thereof in the Formulation A comparison was made between two surfactants:
- the first (example 2) was derived from the esterification between a polyglycerol (DPn=4.6), ricinoleic acid and 12-hydroxystearic acid,
- the second (example 8) was derived from the esterification between a polyglycerol (DPn=10) and a mixture of 12-hydroxystearic acid and ricinoleic acid.

SUMMARY

Example 8: 132 g of 12-hydroxystearic acid, 131 g of ricinoleic acid and 237 g of polyglycerol of DPn=10 were placed in a reactor. 0.085 g of sodium hydroxide was added under stirring. The reaction medium was heated to 215° C. under a nitrogen atmosphere. After 6 hours of reaction, the acid number measured was 1.4 mg KOH/g. The reactor was emptied and the ester was filtered through a polypropylene membrane.

It should be noted that the acid and polyglycerol weights in example 8 were selected so as to obtain a mole ratio of the acids to the polyglycerol that is identical to the mole ratio in example 2.

Performance Levels and Formulations

These two products (examples 2 and 8) were implemented in a water-in-oil formula containing pigments in the manner described below:

| Phase | Ingredients | Weight percentage |
|---|---|---|
| Oil | Surfactant in example 2 or 8 | 5 |
| | Medium-chain triglycerides (MCT) | 3.25 |
| | Lanol 99 | 9.5 |
| | Eutanol G | 9.43 |
| | Preservative | 0.7 |
| | Yellow pigment | 9.3 |
| | White pigment | 1.12 |
| | Red pigment | 0.5 |
| Water | Water | 54.2 |
| | Glycerin | 5 |
| | NaCl | 1 |
| | MgSO$_4$ | 1 |

The Preparation Protocol for the Formulae was as Follows:

The surfactant was dissolved in the oil phase and the two salts (NaCl and MgSO$_4$) were dissolved in water. The two phases were then heated to 75° C. in a water bath. Once the temperature was reached, the oil phase was stirred using a homogeniser at 2,000 rpm. The aqueous phase was then slowly added to the oil phase. Once the addition of water was complete, homogenisation at 2,000 rpm was maintained for 20 minutes. The emulsion was then placed in a cold water bath to reduce the temperature of the emulsion to 30° C. During placement in the cold water bath, the preservative was added drop by drop and stirring was reduced to 1,500 rpm. Stirring was then maintained for 10 minutes. The emulsion was then placed in a container to monitor stability.

The stability of the two formulations was monitored at 40° C.

The results are as follows:

| Test with example | 2 | 8 |
|---|---|---|
| 40° C. | Stable for more than 14 days | Stable for less than 14 days |

The formula containing the surfactant according to example 8 was seen to sediment. The stability of the formula using example 8 is thus lower than that of the formula using the surfactant according to example 2.

The degree of polymerisation (DPn) of the polyglycerol has a significant effect on the performance of the formulations. The use of a polyglycerol having a DPn greater than 6 inhibits the performance of the surfactant. Use of a polyglycerol with a degree of polymerisation DPn of between 4 and 6 is thus preferable, i.e. having a molecular weight of between 314 g/mol and 462 g/mol.

Effect of the Degree of Fatty Acid Content on the Performance Levels of the Formulation A comparison was made between two surfactants:
the first (example 2) was derived from the esterification between a polyglycerol (DPn=4.6), ricinoleic acid and 12-hydroxystearic acid,
the second (example 9) was derived from the esterification between a polyglycerol (DPn=4.6) and ricinoleic acid.

Example 9: 369.5 g of ricinoleic acid and 130.5 g of polyglycerol of DPn=4.6 were placed in a reactor. 0.085 g of sodium hydroxide was added under stirring. The reaction medium was heated to 215° C. under a nitrogen atmosphere. After 6 hours of reaction, the acid number measured was 1.0 mg KOH/g. The reactor was emptied and the ester was filtered through a polypropylene membrane.

It should be noted that the acid and polyglycerol weights in example 9 were selected so as to obtain a mole ratio of the acid to the polyglycerol that is identical to the mole ratio in example 2.

Performance Levels and Formulations

These two products were implemented in a water-in-oil formula containing pigments in the manner described below:

| Phase | Ingredients | Weight percentage |
|---|---|---|
| Oil | Surfactant in example 2 or 9 | 5 |
| | Medium-chain triglycerides (MCT) | 3.25 |
| | Lanol 99 | 9.5 |
| | Eutanol G | 9.43 |
| | Preservative | 0.7 |
| | Yellow pigment | 9.3 |
| | White pigment | 1.12 |
| | Red pigment | 0.5 |
| Water | Water | 54.2 |
| | Glycerin | 5 |
| | NaCl | 1 |
| | MgSO$_4$ | 1 |

The Preparation Protocol for the Formulae was as Follows:

The surfactant was dissolved in the oil phase and the two salts (NaCl and MgSO$_4$) were dissolved in water. The two phases were then heated to 75° C. in a water bath. Once the temperature was reached, the oil phase was stirred using a homogeniser at 2,000 rpm. The aqueous phase was then slowly added to the oil phase. Once the addition of water was complete, homogenisation at 2,000 rpm was maintained for 20 minutes. The emulsion was then placed in a cold water bath to reduce the temperature of the emulsion to 30° C. During placement in the cold water bath, the preservative was added drop by drop and stirring was reduced to 1,500 rpm. Stirring was then maintained for 10 minutes. The emulsion was then placed in a container to monitor stability.

The stability of the two formulations was monitored at 40° C.

The results are as follows:

| Test with example | 2 | 9 |
|---|---|---|
| 40° C. | Stable for more than 14 days | Stable for less than 7 days |

The phases of the formula containing the surfactant according to example 9 were seen to quickly separate. The stability of the formula using example 9 is thus lower than that of the formula using the surfactant according to example 2.

To summarise, the sole use of ricinoleic acid, instead of 12-hydroxystearic acid or a mixture of 12-hydroxystearic acid and ricinoleic acid, during synthesis of the surfactant, results in lower performance levels. The use of 12-hydroxystearic acid or a mixture of the two ricinoleic and 12-hydroxystearic acids is thus preferable to the use of ricinoleic acid alone.

The invention claimed is:

1. A water-in-oil surfactant consisting of a mixture of compounds of formula (I):

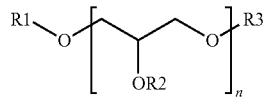
(I)

wherein the compounds of formula (I) have an average degree of polymerisation n of between 4 and 6,
R1, R2 and R3 being, independently of one another, a hydrogen atom,
12-hydroxystearic acid, a mixture of 12-hydroxystearic acid and ricinoleic acid, or an R4 group,
R4 being a group C(=O)—(R5)-CH[(CH$_2$)$_5$—CH$_3$]—O—{C(=O)—(R5)-CH[(CH$_2$)$_5$—CH$_3$]—O}$_p$C(=O)—(R5)-CH[(CH$_2$)$_5$—CH$_3$]—OH where p=0 to 5,
R5 being a mixture of the groups (CH$_2$)$_{10}$ and (CH$_2$)$_7$—(CH=CH)—CH$_2$, and wherein at least one of the R1, R2 and R3 groups is an R4 group.

2. The surfactant according to claim 1, wherein the compounds of formula (I) have an average degree of polymerisation n of between 4 and 5.

3. The surfactant according to claim 1, wherein the surfactant has a HLB value of between 1 and 6.

4. The surfactant according to claim 1, wherein p=0 to 3.

5. The surfactant according to claim 1, wherein R2 is a hydrogen atom.

6. The surfactant according to claim 1, wherein R5 is a mixture of the groups (CH$_2$)$_{10}$ and (CH$_2$)$_7$—(CH=CH)—CH$_2$, said surfactant having a ratio of the number of groups R5=(CH$_2$)$_{10}$ to the number of groups R5=(CH$_2$)$_7$—(CH=CH)—CH$_2$ of between 0.5 and 4.

7. The surfactant according to claim 1, wherein
the R1 and R3 groups are R4 groups of the formula C(=O)—(CH$_2$)$_{10}$—CH[(CH$_2$)$_5$—CH$_3$]—O—{C(=O)—(CH$_2$)$_{10}$—CH[(CH$_2$)$_5$—CH$_3$]—O}$_p$C(=O)—(CH$_2$)$_{10}$—CH[(CH$_2$)$_5$—CH$_3$]—OH
or
the R1 and R3 groups are R4 groups that are a mixture of groups of the formula C(=O)—(CH$_2$)$_{10}$—CH[(CH$_2$)$_5$—CH$_3$]—O—{C(=O)—(CH$_2$)$_{10}$—CH[(CH$_2$)$_5$—CH$_3$]—O}$_p$C(=O)—(CH$_2$)$_{10}$—CH[(CH$_2$)$_5$—CH$_3$]—OH and of the formula C(=O)—(CH$_2$)$_7$—(CH=CH)—CH$_2$—CH[(CH$_2$)$_5$—CH$_3$]—O—{C(=O)—(CH$_2$)$_7$—(CH=CH)—CH$_2$—CH[(CH$_2$)$_5$—CH$_3$]—O}$_p$C(=O)—(CH$_2$)$_7$—(CH=CH)—CH$_2$—CH[(CH$_2$)$_5$—CH$_3$]—OH.

8. A method for preparing the surfactant according to claim 1 comprising performing an esterification reaction between polyglycerol and at least one carboxylic acid,
the carboxylic acid being 12-hydroxystearic acid or a mixture of 12-hydroxystearic acid and ricinoleic acid.

9. The method according to claim 8, wherein the esterification reaction is carried out in the presence of a polyglycerol/carboxylic acid(s) mole ratio of between 0.5 and 0.25.

10. The method according to claim 8, wherein the esterification reaction is carried out at a temperature of between 185 and 235° C.

11. A surfactant composition comprising a water-in-oil surfactant consisting of a mixture of compounds of formula (I):

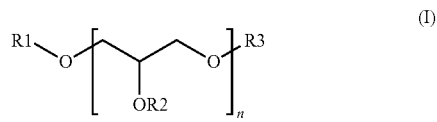
(I)

wherein the compound of formula (I) has an average degree of polymerisation n of between 4 and 6,
R1, R2 and R3 being, independently of one another, a hydrogen atom, 12-hydroxystearic acid, a mixture of 12-hydroxystearic acid and ricinoleic acid, or an R4 group,
R4 being a group C(=O)—(R5)-CH[(CH$_2$)$_5$—CH$_3$]—O—{C(=O)—(R5)-CH[(CH$_2$)$_5$—CH$_3$]—O}$_p$C(=O)—(R5)-CH[(CH$_2$)$_5$—CH$_3$]—OH where p=0 to 5,
R5 being a mixture of the groups (CH$_2$)$_{10}$ and (CH$_2$)$_7$—(CH=CH)—CH$_2$,
and wherein at least one of the R1, R2 and R3 groups is an R4 group.

12. A cosmetic composition comprising a water-in-oil surfactant consisting of a mixture of compounds of formula (I):

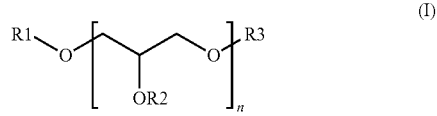
(I)

wherein the compounds of formula (I) have an average degree of polymerisation n of between 4 and 6,
R1, R2 and R3 being, independently of one another, a hydrogen atom, 12-hydroxystearic acid, a mixture of 12-hydroxystearic acid and ricinoleic acid, or an R4 group,
R4 being a group C(=O)—(R5)-CH[(CH$_2$)$_5$—CH$_3$]—O—{C(=O)—(R5)-CH[(CH$_2$)$_5$—CH$_3$]—O}$_p$C(=O)—(R5)-CH[(CH$_2$)$_5$—CH$_3$]—OH where p=0 to 5,
R5 being a mixture of the groups (CH$_2$)$_{10}$ and (CH$_2$)$_7$—(CH=CH)—CH$_2$,
and wherein at least one of the R1, R2 and R3 groups is an R4 group.

13. The surfactant according to claim 1, wherein the compounds of formula (I) have an average degree of polymerisation n of from 4.5 to 5.

14. The surfactant according to claim 1, wherein the surfactant has a HLB value of between 2 and 6.

15. The surfactant according to claim 1, wherein the surfactant has a HLB value of between 3 and 5.

16. The surfactant according to claim 2, wherein the surfactant has a HLB value of between 3 and 5.

17. The surfactant according to claim 1, wherein p=0 to 2.

18. The surfactant according to claim 1, wherein R5 is a mixture of the groups (CH$_2$)$_{10}$ and (CH$_2$)$_7$—(CH=CH)—CH$_2$, said surfactant having a ratio of the number of groups R5=(CH$_2$)$_{10}$ to the number of groups R5=(CH$_2$)$_7$—(CH=CH)—CH$_2$ of between 0.75 and 2.

19. The method according to claim 8, wherein the esterification reaction is carried out in the presence of a polyglycerol/carboxylic acid(s) mole ratio of between 1 and 0.15.

20. The method according to claim 8, wherein the esterification reaction is carried out at a temperature of between 190 and 220° C.

\* \* \* \* \*